(12) United States Patent
Fujiwara et al.

(10) Patent No.: US 6,365,776 B1
(45) Date of Patent: Apr. 2, 2002

(54) PROCESS FOR PRODUCING AROMATIC AMINES

(75) Inventors: Mitsuhiko Fujiwara; Ken Suzuki; Tohru Kobayashi; Yoji Hori; Toshimitsu Hagiwara, all of Kanagawa (JP)

(73) Assignee: Takasago International Corporation, Tokyo (JP)

(*) Notice: Subject to any disclaimer, the term of this patent is extended or adjusted under 35 U.S.C. 154(b) by 0 days.

(21) Appl. No.: 09/946,468

(22) Filed: Sep. 6, 2001

(30) Foreign Application Priority Data

Sep. 7, 2000 (JP) .............................................. P-271599

(51) Int. Cl.⁷ ............................................ C07C 211/00
(52) U.S. Cl. ...................... 564/433; 564/432; 564/435; 564/407; 564/405; 564/307
(58) Field of Search ................................ 564/307, 405, 564/407, 435, 433, 432

(56) References Cited

FOREIGN PATENT DOCUMENTS

| EP | 0 274 795 A2 | 7/1988 |
| EP | WO 68/56839 | 12/1998 |

OTHER PUBLICATIONS

Minoru Hayashi et al., "Phosphine Sulfides: Novel Effective Ligands for the Palladium–Catalyzed Bisalkoxycarbonylation of Olefins", Tetrahedreon Letters; 39, (1998), pp. 7529–7532.

*Primary Examiner*—Samuel Barts
(74) *Attorney, Agent, or Firm*—Sughrue Mion, PLLC

(57) ABSTRACT

The present invention provides an activator in arylamination using a palladium compound as a catalyst, which is superior to conventional phosphines in stability and performance. With the phosphine sulfide as an activator, an arylamination reaction achieves improved selectivity to produce a desired aromatic amine in an obviously increased yield as compared with a reaction using the corresponding phosphine compound. Moreover, the phosphine sulfide of the invention is impervious to oxidation and exists stably in air and therefore sufficiently withstands use on an industrial scale.

6 Claims, No Drawings

PROCESS FOR PRODUCING AROMATIC AMINES

FIELD OF THE INVENTION

This invention relates to a process for producing aromatic amines by the reaction between aromatic compounds having a releasable group and amines. More particularly, it relates to a process for producing an aromatic amine by the reaction between an aromatic compound having a releasable group and an amine in the presence of a palladium catalyst having a phosphine sulfide as a ligand. The aromatic amines obtained by the process are useful as a material of organic electronic materials and pharmaceuticals.

BACKGROUND ART

A number of proposals have been reported on production of aromatic amines by condensation of an aryl halide and an amine. For example, the latest development of an Ullmann reaction in the presence of a copper catalyst is reported in *JOC*, p. 670 (1999). The feature of this reaction, which is also a demerit, lies in that only an iodide, which is highly reactive, is usable as an aryl halide so that a less expensive bromide cannot be used.

On the other hand, it is known that use of a palladium compound as a catalyst enables use of either a bromide or a chloride as an aryl halide substrate. For example, Buchwald et al. and Hartwig et al. show methods in which a phosphine is used as an activator (see *Acc. Chem. Res.*, vol. 31, pp 805 and 852 (1998)). However, phosphines as an activator are generally susceptible to oxidation and need care in handling.

The phosphine's susceptibility to oxidation makes the arylamination reaction using a phosphine as an activator very sensitive to the type or quality of the phosphine, and a more stable activator that can take the place of a phosphine has been sought. Accordingly, an object of the present invention is to provide a more stable activator in arylamination using a palladium compound as a catalyst.

SUMMARY OF THE INVENTION

As a result of extensive investigation, the inventors of the present invention have found that a phosphine sulfide which is impervious to oxidation acts as an effective ligand activating a palladium catalyst thereby to activate the arylamination reaction significantly. The present invention has been completed based on this finding.

The present invention provides a process of producing an aromatic amine comprising allowing an aromatic compound having a releasable group to react with an amine in the presence of a phosphine sulfide and a palladium compound, for example, as described below.

(1) A process for producing an aromatic amine comprising allowing an aromatic compound having a releasable group to react with an amine in the presence of a phosphine sulfide and a palladium compound.

(2) A process according to (1) above, wherein the reaction is carried out in the presence of a base.

(3) A process according to (1) or (2) above, wherein said releasable group is a halogen atom, a trifluoromethanesulfonyloxy group, a methanesulfonyloxy group or a p-toluenesulfonyloxy group.

(4) A process according to (1) or (2) above, wherein said releasable group is a halogen atom.

(5) A process according to any one of (1) to (4) above, wherein said phosphine sulfide is a compound represented by formula (I):

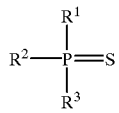

wherein $R^1$, $R^2$, $R^3$ each represent a substituted or unsubstituted alkyl group, a substituted or unsubstituted cycloalkyl group, a substituted or unsubstituted alkenyl group or a substituted or unsubstituted aryl group; and any two of $R^1$, $R^2$ and $R^3$ may be connected to each other to form an alkylene chain; provided that at least one of $R^1$, $R^2$ and $R^3$ is an alkenyl group or an aryl group.

(6) A process according to any one of (1) to (5) above, wherein said amine is a primary amine, a secondary amine, an imine or an amide.

Compared with the reaction using a phosphine as an activator, the reaction using a phosphine sulfide as an activator shows an apparently improved selectivity to provide a desired aromatic amine in a noticeably increased yield. This fact obviously denies the assumption that a phosphine sulfide may be reduced to phosphine in the reaction system to participate in the reaction.

The phosphine sulfide which can be used in the present invention includes compounds represented by formula (I):

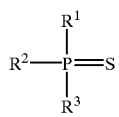

wherein $R^1$, $R^2$, $R^3$ each represent a substituted or unsubstituted alkyl group, a substituted or unsubstituted cycloalkyl group, a substituted or unsubstituted alkenyl group or a substituted or unsubstituted aryl group; and any two of $R^1$, $R^2$ and $R^3$ may be connected to each other to form an alkylene chain; provided that at least one of $R^1$, $R^2$ and $R^3$ is an alkenyl group or an aryl group.

In formula (I), the alkyl group, which may be substituted or unsubstituted, represented by $R^1$, $R^2$ and $R^3$ includes a straight-chain or branched alkyl group having 1 to 20, preferably 1 to 10, still preferably 1 to 6, carbon atoms, such as methyl, ethyl, propyl, isopropyl, butyl, isobutyl, sec-butyl, t-butyl, pentyl and hexyl. The alkyl group may have any substituent(s) that would not adversely affect the arylamination reaction.

The cycloalkyl group, which may be substituted or unsubstituted, includes a monocyclic, polycyclic or condensed cycloalkyl group having 3 to 30, preferably 3 to 20, still preferably 3 to 10, carbon atoms, such as cyclopropyl, cyclopentyl, cyclohexyl and cyclooctyl. The cycloalkyl group may have any substituent(s) that would not adversely affect the arylamination reaction.

The alkenyl group includes a vinyl group, an allyl group, etc., each of which may be substituted with the above-described alkyl group, a phenyl group, etc. Specific examples of the alkenyl group are vinyl, allyl, 1-methyl-2,2-diphenylvinyl, and 1,2,2-triphenylvinyl.

The aryl group, which may be substituted or unsubstituted, includes a monocyclic, polycyclic or condensed aromatic hydrocarbon group having 6 to 30, preferably 6 to 20, still preferably 6 to 15, carbon atoms, such as phenyl, tolyl, xylyl, naphthyl, methylnaphthyl, and biphenyl. The aryl group can have any substituent(s) that do not cause hindrance to the arylamination reaction.

Examples of the substituent(s) of the substituted alkyl group, substituted cycloalkyl group, substituted alkenyl group, and substituted aryl group include alkyl groups, cycloalkyl groups, alkenyl groups, aryl groups, alkoxy groups, tertiary amino groups, and aryloxy groups, preferably $C_{1-20}$ alkyl groups, $C_{3-30}$ cycloalkyl groups, $C_{2-30}$ alkenyl groups, $C_{6-20}$ aryl groups, $C_{1-20}$ alkoxy groups, $C_{2-20}$ tertiary amino groups, and $C_{6-20}$ aryloxy groups. The tertiary amino groups are preferably the groups represented by $-N(R^4)(R^5)$ wherein each of $R^4$ and $R^5$ independently represents an alkyl group, a cycloalkyl group, an alkenyl group, or an aryl group.

Specific examples of the phosphine sulfides which can be used in the present invention are triphenylphosphine sulfide, P,P-dicyclohexyl-o-biphenylphosphine sulfide, P,P-di-t-butyl-o-biphenylphosphine sulfide, P,P-dicyclohexyl-(1-methyl-2,2-diphenylvinyl)phosphine sulfide, P,P-di-t-butyl-(1-methyl-2,2-diphenylvinyl)phosphine sulfide, P,P-dicyclohexyl-(1,2,2-triphenylvinyl)phosphine sulfide, and P,P-di-t-butyl-(1,2,2-triphenylvinyl)phosphine sulfide.

These compounds are commercially available, which can be used in the invention, or easily obtainable by the reaction between a corresponding phosphine compound and sulfur (see *J. Chem. Soc., Dalton Trans.,* No. 1973, p. 1024).

The aromatic compound having a releasable group which can be used in the invention includes compounds represented by formula (II):

$$ArX^1 \qquad (II)$$

wherein Ar represents a substituted or unsubstituted aryl group or a substituted or unsubstituted heteroaryl group; and $X^1$ represents a halogen atom, a trifluoromethanesulfonyloxy group, a methanesulfonyloxy group or a p-toluenesulfonyloxy group.

In formula (II), the aryl group Ar, which may be substituted or unsubstituted, includes a monocyclic, polycyclic or condensed aromatic hydrocarbon group having 6 to 30, preferably 6 to 20, still preferably 6 to 15, carbon atoms, such as phenyl, tolyl, xylyl, naphthyl, methylnaphthyl, anthryl, phenathryl and biphenyl. The aryl group can have any substituent(s) that do not cause hindrance to the arylamination reaction. The substituents include, but are not limited to, a hydroxyl group, an alkoxy group (e.g., methoxy, ethoxy, propoxy or butoxy), a hydroxyalkyl group (e.g., hydroxymethyl or hydroxyethyl), a trifluoromethyl group, a trifluoromethoxy group, and a methylenedioxy group.

The heteroaryl group, which may be substituted or unsubstituted, includes a 5- to 20-membered, preferably 5- to 10-membered, still preferably 5- to 7-membered unsaturated monocyclic, polycyclic or condensed cyclic group containing at least one hetero atom selected from nitrogen, oxygen and sulfur, which may be condensed with a carbon ring, e.g., a cycloalkyl group, a cycloalkenyl group or an aryl group. Specific examples of the heteroaryl group are pyridyl, thienyl, thiazolyl, furyl, imidazolyl, indolyl, quinolyl, and pyrimidinyl.

The substituents the heteroaryl group may have include, but are not limited to, the above-recited substituents the aryl group may have. Any substituents that do not adversely affect the reaction can be present.

The aromatic compound having a releasable group which can be used in the invention includes, but is not limited to, aryl bromides, such as bromobenzene, o-bromoanisole, m-bromoanisole, p-bromoanisole, o-bromotoluene, m-bromotoluene, p-bromotoluene, o-bromophenol, m-bromophenol, p-bromophenol, 2-bromobenzotrifluoride, 3-bromobenzotrifluoride, 4-bromobenzotrifluoride, 1-bromo-2,4-dimethoxybenzene, 1-bromo-2,5-dimethoxybenzene, 2-bromophenethyl alcohol, 3-bromophenethyl alcohol, 4-bromophenethyl alcohol, 5-bromo-1,2,4-trimethylbenzene, 2-bromo-m-xylene, 2-bromo-p-xylene, 3-bromo-o-xylene, 4-bromo-o-xylene, 4-bromo-m-xylene, 5-bromo-m-xylene, 1-bromo-3-(trifluoromethoxy)benzene, 1-bromo-4-(trifluoromethoxy) benzene, 2-bromobiphenyl, 3-bromobiphenyl, 4-bromobiphenyl, 4-bromo-1,2-(methylenedioxy)benzene, 1-bromonaphthalene, 2-bromonaphthalene, 1-bromo-2-methylnaphthalene, 1-bromo-4-methylnaphthalene, 1,4-dibromonaphthalene, 4,4'-dibromobiphenyl, 2-bromothiophene, 3-bromothiophene, 2-bromopyridine, 3-bromopyridine, 4-bromopyridine, 9-bromophenanthrene, 2-bromofuran, and 3-bromofuran; aryl chlorides, such as chlorobenzene o-chloroanisole, m-chloroanisole, p-chloroanisole, o-chlorotoluene, m-chlorotoluene, p-chlorotoluene, o-chlorophenol, m-chlorophenol, p-chlorophenol, 2-chlorobenzotrifluoride, 3-chlorobenzotrifluoride, 4-chlorobenzotrifluoride, 1-chloro-2,4-dimethoxybenzene, 1-chloro-2,5-dimethoxybenzene, 2-chlorophenethyl alcohol, 3-chlorophenethyl alcohol, 4-chlorophenethyl alcohol, 5-chloro-1,2,4-trimethylbenzene, 2-chloro-m-xylene, 2-chloro-p-xylene, 3-chloro-o-xylene, 4-chloro-o-xylene, 4-chloro-m-xylene, 5-chloro-m-xylene, 1-chloro-3-(trifluoromethoxy)benzene, 1-chloro-4-(trifluoromethoxy) benzene, 2-chlorobiphenyl, 3-chlorobiphenyl, 4-chlorobiphenyl, 1-chloronaphthalene, 2-chloronaphthalene, 1-chloro-2-methylnaphthalene, 1-chloro-4-methylnaphthalene, 1,4-dichloronaphthalene, 4,4'-dichlorobiphenyl, 2-chlorothiophene, 3-chlorothiophene, 2-chloropyridine, 3-chloropyridine, 4-chloropyridine, 9-chlorophenanthrene, 2-chlorofuran, and 3-chlorofuran; aryl iodides, such as iodobenzene, o-iodoanisole, m-iodoanisole, p-iodoanisole, o-iodotoluene, m-iodotoluene, p-iodotoluene, o-iodophenol, m-iodophenol, p-iodophenol, 2-iodobenzotrifluoride, 3-iodobenzotrifluoride, 4-iodobenzotrifluoride, 1-iodo-2,4-dimethoxybenzene, 1-iodo-2,5-dimethoxybenzene, 2-iodophenethyl alcohol, 3-iodophenethyl alcohol, 4-iodophenethyl alcohol, 5-iodo-1,2,4-trimethylbenzene, 2-iodo-m-xylene, 2-iodo-p-xylene, 3-iodo-o-xylene, 4-iodo-o-xylene, 4-iodo-m-xylene, 5-iodo-m-xylene, 1-iodo-3-(trifluoromethoxy)benzene, 1-iodo-4-(trifluoromethoxy) benzene, 2-iodobiphenyl, 3-iodobiphenyl, 4-iodobiphenyl, 1-iodonaphthalene, 2-iodonaphthalene, 1-iodo-2-methylnaphthalene, 1-iodo-4-methylnaphthalene, 1,4-diiodonaphthalene, 4,4'-diiodobiphenyl, 2-iodothiophene, 3-iodothiophene, 2-iodopyridine, 3-iodopyridine, 4-iodopyridine, 9-iodophenanthrene, 2-iodofuran, and 3-iodofuran; aryl fluorides, such as fluorobenzene, o-fluoroanisole, m-fluoroanisole, p-fluoroanisole, o-fluorotoluene, m-fluorotoluene, p-fluorotoluene, o-fluorophenol, m-fluorophenol, p-fluorophenol, 2-fluorobenzotrifluoride, 3-fluorobenzotrifluoride, 4-fluorobenzotrifluoride, 1-fluoro-2,4-dimethoxybenzene, 1-fluoro-2,5-dimethoxybenzene, 2-fluorophenethyl alcohol, 3-fluorophenethyl alcohol, 4-fluorophenethyl alcohol, 5-fluoro-1,2,4-trimethylbenzene, 2-fluoro-m-xylene, 2-fluoro-p-xylene, 3-fluoro-o-xylene, 4-fluoro-o-xylene, 4-fluoro-m-xylene, 5-fluoro-m-xylene, 1-fluoro-3-(trifluoromethoxy)benzene, 1-fluoro-4-(trifluoromethoxy) benzene, 2-fluorobiphenyl, 3-fluorobiphenyl, 4-fluorobiphenyl, 4-fluoro-1,2-(methylenedioxy)benzene, 1-fluoronaphthalene, 2-fluoronaphthalene, 1-fluoro-2-methylnaphthalene, 1-fluoro-4-methylnaphthalene, 1,4-difluoronaphthalene, 4,4'-difluorobiphenyl, 2-fluorothiophene, 3-fluorothiophene, 2-fluoropyridine, 3-fluoropyridine, 4-fluoropyridine, 9-fluorophenanthrene, 2-fluorofuran, and 3-fluorofuran; aryltrifluoromethanesulfonyl oxides, such as trifluoromethanesulfonyloxybenzene, o-trifluoromethanesulfonyloxyanisole, m-trifluoromethanesulfonyloxyanisole, p-trifluoromethanesulfonyloxyanisole, o-trifluoromethanesulfonyloxytoluene, m-trifluoromethanesulfonyloxytoluene, p-trifluoromethanesulfonyloxytoluene, o-trifluoromethanesulfonyloxyphenol, m-trifluoromethanesulfonyloxyphenol, p-trifluoromethanesulfonyloxyphenol, 2-trifluoromethanesulfonyloxybenzotrifluoride, 3-trifluoromethanesulfonyloxybenzotrifluoride, 4-trifluoromethanesulfonyloxybenzotrifluoride, 1-trifluoromethanesulfonyloxy-2,4-dimethoxybenzene, 1-trifluoromethanesulfonyloxy-2,5-dimethoxybenzene, 2-trifluoromethanesulfonyloxyphenethyl alcohol, 3-trifluoromethanesulfonyloxyphenethyl alcohol, 4-trifluoromethanesulfonyloxyphenethyl alcohol, 5-trifluoromethanesulfonyloxy-1,2,4-trimethylbenzene, 2-trifluoromethanesulfonyloxy-m-xylene, 2-trifluoromethanesulfonyloxy-p-xylene, 3-trifluoromethanesulfonyloxy-o-xylene, 4-trifluoromethanesulfonyloxy-o-xylene, 4-trifluoromethanesulfonyloxy-m-xylene, 5-trifluoromethanesulfonyloxy-m-xylene, 1-trifluoromethanesulfonyloxy-3-(trifluoromethoxy)benzene, 1-trifluoromethanesulfonyloxy-4-(trifluoromethoxy)benzene, 2-trifluoromethanesulfonyloxybiphenyl, 3-trifluoromethanesulfonyloxybiphenyl, 4-trifluoromethanesulfonyloxybiphenyl, 4-trifluoromethanesulfonyloxy-1,2-(methylenedioxy)benzene, 1-trifluoromethanesulfonyloxynaphthalene, 2-trifluoromethanesulfonyloxynaphthalene, 1-trifluoromethanesulfonyloxy-2-methylnaphthalene, 1-trifluoromethanesulfonyloxy-4-methylnaphthalene, 1,4-ditrifluoromethanesulfonyloxynaphthalene, 4,4'-ditrifluoromethanesulfonyloxybiphenyl, 2-trifluoromethanesulfonyloxythiophene, 3-trifluoromethanesulfonyloxythiophene, 2-trifluoromethanesulfonyloxypyridine, 3-trifluoromethanesulfonyloxypyridine, 4-trifluoromethanesulfonyloxypyridine, 9-trifluoromethanesulfonyloxyphenathrene, 2-trifluoromethanesulfonyloxyfuran, and 3-trifluoromethanesulfonyloxyfuran; arylmethanesulfonyl oxides, such as methanesulfonyloxybenzene, o-methanesulfonyloxyanisole, m-methanesulfonyloxyanisole, p-methanesulfonyloxyanisole, o-methanesulfonyloxytoluene, m-methanesulfonyloxytoluene, p-methanesulfonyloxytoluene, o-methanesulfonyloxyphenol, m-methanesulfonyloxyphenol, p-methanesulfonyloxyphenol, 2-methanesulfonyloxybenzotrifluoride, 3-methanesulfonyloxybenzotrifluoride, 4-methanesulfonyloxybenzotrifluoride, 1-methanesulfonyloxy-2,4-dimethoxybenzene, 1-methanesulfonyloxy-2,5-dimethoxybenzene, 2-methanesulfonyloxyphenethyl alcohol, 3-methanesulfonyloxyphenethyl alcohol, 4-methanesulfonyloxyphenethyl alcohol, 5-methanesulfonyloxy-1,2,4-trimethylbenzene, 2-methanesulfonyloxy-m-xylene, 2-methanesulfonyloxy-p-xylene, 3-methanesulfonyloxy-o-xylene, 4-methanesulfonyloxy-o-xylene, 4-methanesulfonyloxy-m-xylene, 5-methanesulfonyloxy-m-xylene, 1-methanesulfonyloxy-3-(trifluoromethoxy)benzene, 1-methanesulfonyloxy-4-(trifluoromethoxy)benzene, 2-methanesulfonyloxybiphenyl, 3-methanesulfonyloxybiphenyl, 4-methanesulfonyloxybiphenyl, 4-methanesulfonyloxy-1,2-(methylenedioxy)benzene, 1-methanesulfonyloxynaphthalene, 2-methanesulfonyloxynaphthalene, 1-methanesulfonyloxy-2-methylnaphthalene, 1-methanesulfonyloxy-4-methylnaphthalene, 1,4-dimethanesulfonyloxynaphthalene, 4,4'-dimethanesulfonyloxybiphenyl, 2-methanesulfonyloxythiophene, 3-methanesulfonyloxythiophene, 2-methanesulfonyloxypyridine, 3-methanesulfonyloxypyridine, 4-methanesulfonyloxypyridine, 9-methanesulfonyloxyphenanthrene, 2-methanesulfonyloxyfuran, and 3-methanesulfonyloxyfuran; and aryl-p-toluenesulfonyl oxides, such as p-toluenesulfonyloxybenzene, o-(p-toluenesulfonyloxy)anisole, m-(p-toluenesulfonyloxy)anisole, p-(p-toluenesulfonyloxy)anisole, o-(p-toluenesulfonyloxy)toluene, m-(p-toluenesulfonyloxy)toluene, p-(p-toluenesulfonyloxy)toluene, o-(p-toluenesulfonyloxy)phenol, m-(p-toluenesulfonyloxy)phenol, p-(p-toluenesulfonyloxy)phenol, 2-(p-toluenesulfonyloxy)benzotrifluoride, 3-(p-toluenesulfonyloxy)benzotrifluoride, 4-(p-toluenesulfonyloxy)benzotrifluoride, 1-(p-toluenesulfonyloxy)-2,4-dimethoxybenzene, 1-(p-toluenesulfonyloxy)-2,5-dimethoxybenzene, 2-(p-toluenesulfonyloxy)phenethyl alcohol, 3-(p-toluenesulfonyloxy)phenethyl alcohol, 4-(p-toluenesulfonyloxy)phenethyl alcohol, 5-(p-toluenesulfonyloxy)-1,2,4-trimethylbenzene, 2-(p-toluenesulfonyloxy)-m-xylene, 2-(p-toluenesulfonyloxy)-p-xylene, 3-(p-toluenesulfonyloxy)-o-xylene, 4-(p-toluenesulfonyloxy)-o-xylene, 4-(p-toluenesulfonyloxy)-m-xylene, 5-(p-toluenesulfonyloxy)-m-xylene, 1-(p-toluenesulfonyloxy)-3-(trifluoromethoxy)benzene, 1-(p-toluenesulfonyloxy)-4-(trifluoromethoxy)benzene, 2-(p-toluenesulfonyloxy)biphenyl, 3-(p-toluenesulfonyloxy)biphenyl, 4-(p-toluenesulfonyloxy)biphenyl, 4-(p-toluenesulfonyloxy)-1,2-(methylenedioxy)benzene, 1-(p-toluenesulfonyloxy)naphthalene, 2-(p-toluenesulfonyloxy)naphthalene, 1-(p-toluenesulfonyloxy)-2-methylnaphthalene, 1-(p-toluenesulfonyloxy)-4-methylnaphthalene, 1,4-di(p-toluenesulfonyloxy)naphthalene, 4,4'-di(p-toluenesulfonyloxy)biphenyl, 2-(p-toluenesulfonyloxy)thiophene, 3-(p-toluenesulfonyloxy)thiophene, 2-(p-toluenesulfonyloxy)pyridine, 3-(p-toluenesulfonyloxy)pyridine, 4-(p-toluenesulfonyloxy)pyridine, 9-(p-toluenesulfonyloxy)phenanthrene, 2-(p-toluenesulfonyloxy)furan, and 3-(p-toluenesulfonyloxy)furan.

Additionally, aryl halides having two or more halogen atoms are also useful as an aromatic compound having a releasable group. Such compounds include 1,2- dibromobenzene, 1,3-dibromobenzene, 1,4-dibromobenzene, 9,10-dibromoanthracene, 9,10-dichloroanthracene, 1-bromo-2-fluorobenzene, 1-bromo-3-fluorobenzene, 1-bromo-4-fluorobenzene, 2-bromochlorobenzene, 3-bromochlorobenzene, 4-bromochlorobenzene, 2-bromo-5-chlorotoluene, 3-bromo-4-chlorobenzotrifluoride, 5-bromo-2-chlorobenzotrifluoride, 1-bromo-2,3-dichlorobenzene, 1-bromo-2,6-dichlorobenzene, 1-bromo-3,5-dichlorobenzene, 2-bromo-4-fluorotoluene, 2-bromo-5-fluorotoluene, 3-bromo-4-fluorotoluene, 4-bromo-2-fluorotoluene, and 4-bromo-3-fluorotoluene.

The amine which can be used in the present invention includes primary amines, secondary amines, imines, and amides.

The primary amines include, but are not limited to, aliphatic primary amines, such as ethylamine, propylamine, butylamine, isobutylamine, t-butylamine, pentylamine, cyclopentylamine, hexylamine, cyclohexylamine, heptylamine, and octylamine; and aromatic primary amines, such as aniline, o-fluoroaniline, m-fluoroaniline, p-fluoroaniline, o-anisidine, m-anisidine, p-anisidine, o-toluidine, m-toluidine, p-toluidine, 2-naphthylamine, 2-aminobiphenyl, 4-aminobiphenyl, 3,4-methylenedioxyaniline, m-xylidine, and p-xylidine.

The secondary amines include, but are not limited to, cyclic secondary amines, such as piperazine, 2-methylpiperazine, homopiperazine, N-methylhomopiperazine, 2,6-dimethylpiperazine, N-methylpiperazine, N-ethylpiperazine, N-ethoxycarbonylpiperazine, N-benzylpiperazine, morpholine, 2,6-dimethylmorpholine, piperidine, 2,6-dimethylpiperidine, 3,3-dimethylpiperidine, 3,5-dimethylpiperidine, 2-ethylpiperidine, 4-piperidoneethylene ketal, pyrrolidine, 2,5-dimethylpyrrolidine, carbazole, indole, and indoline; and acyclic secondary amines, such as dimethylamine, diethylamine, and N-methylaniline, N-ethylaniline, N-methylbenzylamine, N-methylphenethylamine or diphenylamine derivatives whose aromatic ring may have a substituent(s). Examples of the substituent(s) on the aromatic ring include alkyl groups, cycloalkyl groups, alkenyl groups, aryl groups, alkoxy groups, tertiary amino groups, and aryloxy groups, preferably $C_{1-20}$ alkyl groups, $C_{3-30}$ cycloalkyl groups, $C_{2-30}$ alkenyl groups, $C_{6-20}$ aryl groups, $C_{1-20}$ alkoxy groups, $C_{2-20}$ tertiary amino groups, and $C_{6-20}$ aryloxy groups. The tertiary amino groups are preferably the groups represented by —N($R^4$)($R^5$) wherein each of $R^4$ and $R^5$ independently represents an alkyl group, a cycloalkyl group, an alkenyl group, or an aryl group.

The imines include, but are not limited to, benzophenoneimine and 4,4'-dimethoxybenzophenone.

The amides include, but are not limited to, 2-azetidinone (β-propiolactam), γ-butyrolactam, δ-valerolactam, ε-caprolactam, acetamide, propionamide, cyclohexylcarboxamide, benzamide, N-methylformamide, N-methylacetamide, N-ethylacetamide, N-methylcyclohexylcarboxamide, and N-methylbenzamide.

While the palladium compound which can be used in the present invention is not particularly limited, one having a low valency is preferred. Palladium (0) salts and complexes are particularly preferred. Palladium (II) compounds or palladium (IV) compounds which are easily reduced in situ to palladium (II) compounds or palladium (0) are useful as well.

Suitable palladium compounds include palladium (IV) compounds, such as sodium hexachloropalladate (IV) tetrahydrate and potassium hexachloropalladate (IV); palladium (II) compounds such, as palladium (II) chloride, palladium (II) bromide, palladium (II) acetate, acetylacetonatopalladium (II), dichlorobisbenzonitrilepalladium (II), dichlorobisacetonitrilepalladium (II), dichlorobis(triphenylphosphine)palladium (II), dichlorotetramminepalladium (II), dichloro(cycloocta-1,5-diene)palladium (II), palladium (II) trifluoroacetate, allylpalladium (II) chloride, and π-allylpalladium (II) chloride dimer; and palladium (0) compounds, such as tris(dibenzylideneacetone)dipalladium (0), tris(dibenzylideneacetone)dipalladium (0) chloroform complex, and tetrakis(triphenylphosphine)palladium (0).

The amination can be carried out in the same manner as reported by Buchwald et al. (see *J. Org. Chem.,* No. 2000, p. 1158).

The amine is used in an amount of 0.5 to 30 mol per mole of the aromatic compound having a releasable group or 0.5 to 10 mol per mole of the releasable group on the nucleus of the aromatic compound. As a matter of course, a smaller amount of the amine results in a lower yield of the aromatic amine, and a larger amount makes recovery of the unreacted amine troublesome. From this standpoint, a preferred amount of the amine is 1 to 10 mol, particularly 1 to 5 mol, per mole of the aromatic compound or 1 to 5 mol, particularly 1 to 3 mol, per mole of the releasable group of the aromatic compound.

The palladium compound is used in an amount of 0.1 to 30 mol %, preferably 0.5 to 20 mol %, still preferably 1 to 10 mol %, per mole of the aromatic compound. The phosphine sulfide is used in an amount of 0.1 to 10 mol, preferably 1 to 7 mol, still preferably 2 to 5 mol, per mole of the palladium compound.

The process according to the present invention is usually carried out in the presence of a base. The base which can be used in the invention is not particularly limited and may be either organic or inorganic. Suitable bases include alkali metal or alkaline earth metal carbonates such as lithium carbonate, sodium carbonate, potassium carbonate, magnesium carbonate, calcium carbonate and barium carbonate; alkali metal phosphates such as lithium phosphate, potassium phosphate and sodium phosphate; and alkali metal alkoxides such as sodium methoxide, sodium ethoxide, potassium methoxide, potassium ethoxide, lithium t-butoxide, sodium t-butoxide, and potassium t-butoxide. Preferred of them are alkali metal alkoxides such as sodium methoxide, sodium ethoxide, potassium methoxide, potassium ethoxide, lithium t-butoxide, sodium t-butoxide, and potassium t-butoxide.

A preferred amount of the base to be used is about 0.5 to 5 mol, particularly about 1 to 3 mol, per mole of the releasable group of the aromatic compound. Less than 0.5 mol of the base tends to result in a reduced yield of the aromatic amine. Use of the base in a large excess brings about no improvement in yield of the aromatic amine, only to make the work-up procedures after the reaction complicated.

The reaction is usually performed in an inert solvent. Any solvent is usable unless the reaction is hindered. Useful solvents include aliphatic hydrocarbons such as pentane, hexane, heptane, and octane; alicyclic hydrocarbons such as cyclohexane and methylcyclohexane; aromatic hydrocarbons, such as benzene, toluene, and xylene; ethers such as diethyl ether, diisopropyl ether, dimethoxyethane, tetrahydrofuran, dioxane, and dioxolane; acetonitrile, dimethylformamide, dimethyl sulfoxide, and hexamethylphosphotriamide. Amongst them preferred are aromatic hydrocarbons such as benzene, toluene, and xylene, and ethers such as diethyl ether, dimethoxyethane, tetrahydrofuran, and dioxane.

In the practice of the process of the invention, (a) the phosphine sulfide, the aromatic compound having a releasable group, the amine compound, the palladium compound, and, if necessary, the base are charged in a reactor all at once, (b) the amine compound is first charged in a reactor together with, if necessary, the base, and the palladium compound, the phosphine sulfide, and the aromatic compound are separately charged therein, (c) the palladium compound and the phosphine sulfide are previously mixed in a reactor to prepare a catalyst, and the amine compound, the aromatic compound and, if necessary, the base are charged therein, or (d) the palladium compound and the phosphine sulfide are previously mixed to prepare a catalyst, and the catalyst, the amine compound, the aromatic compound and, if necessary, the base are separately charged in a reactor. Whichever manner is followed, the results are equal.

The reaction is usually carried out in an inert gas atmosphere, such as nitrogen or argon, under normal pressure or under pressure at 20 to 300° C., preferably 50 to 200° C. The reaction ordinarily completes in several minutes to several tens of hours, which varies depending on the kinds of the aromatic compound, the amine, and the catalyst, the reaction temperature, and the like. After completion of the reaction, the reaction mixture is worked up in usual manner to give a desired aromatic amine.

The present invention will now be illustrated in greater detail with reference to Examples, but it should be understood that the invention is not construed as being limited thereto.

EXAMPLE 1

Into a sealed tube were put 11 mg (0.060 mmol) of allylpalladium chloride, 69 mg (0.23 mmol) of triphenylphosphine sulfide, and 90 mg (0.93 mmol) of sodium t-butoxide. The atmosphere was displaced with argon, and 137 mg (0.81 mmol) of diphenylamine, 188 mg (0.81 mmol) of p-bromobiphenyl, and 2 ml of a toluene solution containing 122 mg of o-terphenyl (for internal standard) were added thereto. The mixture was heated at 100° C. for 2 hours with stirring. After cooling, the reaction mixture was washed with water and analyzed by gas-liquid chromatography (GLC) to find that the diphenylamine conversion was 70% and that the (p-biphenyl)diphenylamine yield was 58%.

Comparative Example 1

Into a sealed tube were put 12 mg (0.065 mol) of allylpalladium chloride, 68 mg (0.26 mmol) of triphenylphosphine, and 89 mg (0.93 mmol) of sodium t-butoxide. The atmosphere was displaced with argon, and 137 mg (0.81 mmol) of diphenylamine, 188 mg (0.81 mmol) of p-bromobiphenyl, and 2 ml of a toluene solution containing 122 mg of o-terphenyl (for internal standard) were added thereto. The mixture was heated at 100° C. for 2 hours with stirring. After cooling, the reaction mixture was washed with water and analyzed by GLC to find that the diphenylamine conversion was 37% and that the (p-biphenyl)diphenylamine yield was 29%.

EXAMPLE 2

The procedures of Example 1 were followed, except for changing the amount of the allylpalladium chloride to 2.5 mol % based on the p-bromobiphenyl and conducting the reaction at 200° C. for 0.75 hours. As a result, the diphenylamine conversion was 69%, and the yield of (p-biphenyl) diphenylamine was 50%.

EXAMPLE 3

The procedures of Example 1 were followed, except for replacing the triphenylphosphine sulfide with P,P-dicyclohexyl-o-biphenylphosphine sulfide, changing the amount of the allylpalladium chloride to 3.6 mol % based on the p-bromobiphenyl and changing the reaction time to 1.5 hours. As a result, the diphenylamine conversion was 79%, and the yield of (p-biphenyl)diphenylamine was 62%.

Comparative Example 2

The procedures of Example 3 were followed, except for replacing the P,P-dicyclohexyl-o-biphenylphosphine sulfide with P,P-dicyclohexyl-o-biphenylphosphine and changing the amount of the allylpalladium chloride to 4.5 mol % based on the p-bromobiphenyl. As a result of GLC analysis, the diphenylamine conversion was 61%, and the yield of (p-biphenyl)diphenylamine was 44%.

EXAMPLE 4

The procedures of Example 1 were followed, except for replacing the triphenylphosphine sulfide with P,P-dicyclohexyl-(1-methyl-2,2-diphenylvinyl)phosphine sulfide, changing the amount of the allylpalladium chloride to 1.6 mol % based on the p-bromobiphenyl and changing the reaction time to 1 hour. As a result of GLC analysis, the diphenylamine conversion was 66%, and the yield of (p-biphenyl)diphenylamine was 50%.

The present invention provides an activator in arylamination using a palladium compound as a catalyst, which is superior to conventional phosphines in stability and performance. With the phosphine sulfide as an activator, an arylamination reaction achieves improved selectivity to produce a desired aromatic amine in an obviously increased yield as compared with a reaction using the corresponding phosphine compound. Moreover, the phosphine sulfide of the invention is impervious to oxidation and exists stably in air and therefore sufficiently withstands use on an industrial scale.

While the invention has been described in detail and with reference to specific embodiments thereof, it will be apparent to one skilled in the art that various changes and modifications can be made therein without departing from the spirit and scope thereof.

This application is based on Japanese patent application No. 2000-271599 filed on Sep. 7, 2000, the entire contents thereof being hereby incorporated by reference.

What is claimed is:

1. A process for producing an aromatic amine comprising allowing an aromatic compound having a releasable group to react with an amine in the presence of a phosphine sulfide and a palladium compound.

2. A process according to claim 1, wherein the reaction is carried out in the presence of a base.

3. A process according to claim 1, wherein said releasable group is a halogen atom, a trifluoromethanesulfonyloxy group, a methanesulfonyloxy group or a p-toluenesulfonyloxy group.

4. A process according to claim 3, wherein said releasable group is a halogen atom.

5. A process according to any one of claims 1 to 4, wherein said phosphine sulfide is a compound represented by formula (I):

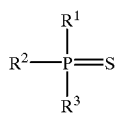

(I)

wherein $R^1$, $R^2$, $R^3$ each represent a substituted or unsubstituted alkyl group, a substituted or unsubstituted cycloalkyl group, a substituted or unsubstituted alkenyl group or a substituted or unsubstituted aryl group; and any two of $R^1$, $R^2$ and $R^3$ may be connected to each other to form an alkylene chain; provided that at least one of $R^1$, $R^2$ and $R^3$ is an alkenyl group or an aryl group.

6. A process according to any one of claims 1 to 4, wherein said amine is a primary amine, a secondary amine, an imine or an amide.

* * * * *